United States Patent
Albrecht et al.

(10) Patent No.: US 11,160,647 B2
(45) Date of Patent: Nov. 2, 2021

(54) IMPLANTS AND METHODS FOR TREATMENTS OF PELVIC CONDITIONS

(71) Applicant: Boston Scientific Scimed, Inc., Maple Grove, MN (US)

(72) Inventors: Thomas A. Albrecht, Edina, MN (US); Ram Kumar Balachandran, Maple Grove, MN (US); John A. Bostrom, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 334 days.

(21) Appl. No.: 15/489,217

(22) Filed: Apr. 17, 2017

(65) Prior Publication Data
US 2017/0304038 A1 Oct. 26, 2017

Related U.S. Application Data (60) Provisional application No. 62/325,267, filed on Apr. 20, 2016.

(51) Int. Cl.
*A61F 2/00* (2006.01)

(52) U.S. Cl.
CPC .......... *A61F 2/0045* (2013.01); *A61F 2/0063* (2013.01); *A61F 2002/0068* (2013.01); *A61F 2220/0075* (2013.01); *A61F 2230/006* (2013.01); *A61F 2240/001* (2013.01); *A61F 2250/0004* (2013.01); *A61F 2250/0012* (2013.01); *A61F 2250/0015* (2013.01); *A61F 2250/0018* (2013.01)

(58) Field of Classification Search
CPC .... A61F 2/0004; A61F 2/0031; A61F 2/0036; A61F 2/0045; A61F 2/0063; A61F 2002/0068; A61F 2002/0081
See application file for complete search history.

(56) References Cited

U.S. PATENT DOCUMENTS

| | | | |
|---|---|---|---|
| 6,652,450 B2 * | 11/2003 | Neisz | A61B 17/0401 600/30 |
| 6,884,212 B2 | 4/2005 | Thierfelder et al. | |
| 7,351,197 B2 | 4/2008 | Montpetit et al. | |

(Continued)

FOREIGN PATENT DOCUMENTS

| | | |
|---|---|---|
| CN | 101128163 A | 2/2008 |
| CN | 105188783 A | 12/2015 |

(Continued)

OTHER PUBLICATIONS

International Search Report and Written Opinion for PCT Patent Application No. PCT/US2017/028089, dated Oct. 20, 2017, 15 pages.

(Continued)

*Primary Examiner* — Carrie R Dorna
(74) *Attorney, Agent, or Firm* — Brake Hughes Bellermann LLP (57) ABSTRACT

Described are surgical implants that include releasable reinforcement, and related methods, particular example implants and methods being useful for treating pelvic tissue, cardiac tissue, and hernia, wherein the releasable reinforcement can be released (removed or disabled) during a surgical procedure to affect a mechanical property of the implant or a portion of the implant.

18 Claims, 7 Drawing Sheets

(56) References Cited

U.S. PATENT DOCUMENTS

| | | |
|---|---|---|
| 7,407,480 B2 | 8/2008 | Staskin et al. |
| 7,422,557 B2 | 9/2008 | Arnal et al. |
| 7,500,945 B2 | 3/2009 | Cox et al. |
| 7,722,527 B2 | 5/2010 | Bouchier et al. |
| 7,905,825 B2 | 3/2011 | Arnal et al. |
| 7,993,261 B2 | 8/2011 | Watschke et al. |
| 8,070,672 B2 | 12/2011 | Arnal et al. |
| 8,109,866 B2 | 2/2012 | Bouchier et al. |
| 8,109,867 B2 | 2/2012 | Rosenblatt |
| 8,211,005 B2 | 7/2012 | Cox et al. |
| 8,388,514 B2 | 3/2013 | Ogdahl et al. |
| 8,517,914 B2 | 8/2013 | Anderson et al. |
| 8,585,576 B2 | 11/2013 | Arnal et al. |
| 8,597,173 B2 | 12/2013 | O'Hern et al. |
| 8,702,585 B2 | 4/2014 | Montpetit et al. |
| 8,720,446 B2 | 5/2014 | Deitch |
| 8,777,836 B2 | 7/2014 | Staskin et al. |
| 8,777,837 B2 | 7/2014 | Ogdahl et al. |
| 8,834,350 B2 | 9/2014 | Chapman et al. |
| 8,932,201 B2 | 1/2015 | Montpetit et al. |
| 8,952,276 B2 | 2/2015 | Lin |
| 8,956,276 B2 | 2/2015 | Young et al. |
| 9,144,426 B2 | 9/2015 | Ogdahl et al. |
| 2002/0028980 A1 | 3/2002 | Thierfelder et al. |
| 2003/0045774 A1 | 3/2003 | Staskin et al. |
| 2005/0038451 A1 | 2/2005 | Rao et al. |
| 2005/0240075 A1* | 10/2005 | Li .................... A61F 2/0045 600/30 |
| 2007/0282160 A1* | 12/2007 | Sheu .................... A61F 2/0045 600/30 |
| 2008/0161837 A1* | 7/2008 | Toso .................... A61F 2/0045 606/151 |
| 2009/0171142 A1 | 7/2009 | Chu |
| 2010/0184805 A1 | 7/2010 | Baldwin et al. |
| 2010/0298630 A1 | 11/2010 | Wignall |
| 2011/0015477 A1 | 1/2011 | Montpetit et al. |
| 2011/0257472 A1 | 10/2011 | Montpetit et al. |
| 2011/0257761 A1* | 10/2011 | Mortarino .......... A61F 2/0063 623/23.72 |
| 2012/0184805 A1 | 7/2012 | Pulliam et al. |
| 2012/0323067 A1 | 12/2012 | Anderson et al. |
| 2013/0109910 A1 | 5/2013 | Alexander et al. |
| 2013/0303840 A1 | 11/2013 | Goldman et al. |
| 2014/0005471 A1 | 1/2014 | Amarasinghe et al. |
| 2014/0073850 A1 | 3/2014 | O'Hern et al. |
| 2014/0155687 A1* | 6/2014 | Goldman .......... A61F 2/0063 600/30 |
| 2014/0228624 A1 | 8/2014 | Montpetit et al. |
| 2014/0276995 A1 | 9/2014 | Lau et al. |
| 2014/0277576 A1 | 9/2014 | Landgrebe et al. |
| 2014/0309485 A1 | 10/2014 | Ogdahl et al. |
| 2014/0357941 A1 | 12/2014 | Chapman et al. |
| 2015/0057491 A1 | 2/2015 | Goddard et al. |
| 2015/0112123 A1 | 4/2015 | Montpetit et al. |
| 2015/0374408 A1 | 12/2015 | Ogdahl et al. |
| 2016/0022404 A1* | 1/2016 | Viker .................... A61F 2/0045 600/37 |

FOREIGN PATENT DOCUMENTS

| | | |
|---|---|---|
| JP | 2004526483 A | 9/2004 |
| WO | 2005110243 A2 | 11/2005 |
| WO | 2014/140612 A2 | 9/2014 |
| WO | 2014149612 A1 | 9/2014 |

OTHER PUBLICATIONS

Second Office Action for Chinese Application No. 201780024325.5 (with English Translation), dated Sep. 25, 2020, 11 pages.

* cited by examiner

IMPLANTS AND METHODS FOR TREATMENTS OF PELVIC CONDITIONS

CROSS-REFERENCE TO RELATED APPLICATION

This application is a Nonprovisional of, and claims priority to, U.S. Patent Application No. 62/325,267, filed on Apr. 20, 2016, entitled "Implants and Methods for Treatments of Pelvic Conditions", which is incorporated by reference herein in its entirety.

FIELD OF THE INVENTION

The present invention relates to sacral colpopexy methods for treating vaginal prolapse conditions by use of adjustable implants to produce differential tensioning of non-apical vaginal tissue, and also to certain particular adjustable implants useful in such sacral colpopexy procedures.

BACKGROUND

Pelvic health for men and women is a medical area of increasing importance, due at least in part to an aging population. Examples of common pelvic ailments include incontinence (e.g., urinary or fecal), pelvic tissue prolapse (e.g., female vaginal prolapse), and conditions of the pelvic floor. Specific vaginal prolapse conditions include non-apical conditions such as cystocele and rectocele, as well as vaginal vault prolapse. Pelvic disorders such as these can result from weakness or damage to normal pelvic support systems.

A form of non-apical prolapse is anterior vaginal prolapse, e.g., cystocele. Rectocele is a form of non-apical posterior vaginal prolapse. An enterocele is a vaginal hernia in which the peritoneal sac containing a portion of the small bowel extends into the rectovaginal space. Apical prolapse, also referred to as vaginal vault prolapse, is a distension of (i.e., prolapse of) the vaginal apex or "vaginal vault." In its severest forms, vaginal vault prolapse can result in the distension of the vaginal apex outside of the vagina. Vaginal vault prolapse often occurs in combination with another form of prolapse such as a rectocele, cystocele, or enterocele.

Some current methods of treating vaginal vault prolapse include sacrocolpopexy (aka "sacral colpopexy" or "SCP"), which includes the use of a surgical implant to suspend vaginal tissue by connecting the tissue to a sacrum. Examples of relevant procedures and implants are described in patent documents that include Patent space. Apical prolapse, also referred to as vaginal vault prolapse, is a distension of (i.e., prolapse of) the vaginal apex or "vaginal vault." In its severest forms, vaginal vault prolapse can result in the distension of the vaginal apex outside of the vagina. Vaginal vault prolapse often occurs in combination with another form of prolapse such as a rectocele, cystocele, or enterocele.

Some current methods of treating vaginal vault prolapse include sacrocolpopexy (aka "sacral colpopexy" or "SCP"), which includes the use of a surgical implant to suspend vaginal tissue by connecting the tissue to a sacrum. Examples of relevant procedures and implants are described in patent documents that include Patent Application Publications 2002/0028980; 2010/0184805; 2014/0005471; 2015/0057491; and U.S. Pat. Nos. 8,109,867; 8,720,446; and 8,956,276.

Sacrocolpopexy procedures are known. They involve surgically removing the uterus of the patient (hysterectomy) if the uterus is present, followed by suspension of the vaginal walls or apex from the sacrum using a synthetic mesh. The procedure places the vaginal apex back in its anatomical position, and retains the tissue in place by means of the synthetic mesh.

According to certain SCP procedures, the surgical implant is a mesh that is preformed into the shape of a "Y," having two anterior leafs connected at a single junction to a single posterior or distal leaf. In use, the two anterior "leafs" (or "arms" or "appendages" of the "Y"-shaped implant) are surgically secured to tissue of an anterior vaginal apex, and to posterior tissue of the vaginal apex. The third portion of the Y-shaped mesh (i.e., the sacral leaf or sacral tail) is secured in a posterior direction to tissue at or near a sacrum, such as at a patient's anterior longitudinal ligament. A number of Y-shaped surgical implant products are currently sold commercially, examples including products from BARD (Alyte implant), ASTORA (Y-mesh implant), Coloplast (Restorelle implant), Boston Scientific (Upsylon implant), and Caldera (Vertessa implant).

A sacrocolpopexy procedure for treating apical prolapse, as typically performed using a commercially available preformed non-adjustable Y-type implant, includes initial steps of suturing the two vaginal portions (leafs, appendages) of the implant to tissue of the anterior and posterior vaginal apex. After attachment of the vaginal leafs to the vaginal tissues, a desired tension, i.e., an amount of tension required to suspend the vaginal tissue from the sacrum, is identified, and the sacral tail of the implant is surgically attached at or near the sacrum. Determining the right amount of tension to place on the implant through the sacral leaf is important to the success of the procedure. Too much tension can result in complications like urinary incontinence. Too little tension can cause recurring prolapse.

Many implants known for treating pelvic conditions (e.g., SCP procedures, incontinence), and other implants known for treating other soft tissue conditions, are relatively uniform in their mechanical properties. Others implants have been described as having different implant portions that exhibit different physical or mechanical features (see PCT patent publication 2014/140612; PCT/US2014/019871).

In the surgical arts, there is ongoing interest in providing improved implantable devices that will provide better therapeutic effect for patients.

SUMMARY

Current and previous surgical implants used for repairing or treating soft tissue, or for treating a condition related to damaged or weakened soft tissue, are constructed to exhibit substantially uniform mechanical properties over the entirety of the implant, or at least over the area of each of the separate portions of the implant. For example, according to known implants, the portions of the implant that are designed to engage and support soft tissue (sometimes referred to as a "tissue support portion" of an implant) are essentially uniform in their makeup and mechanical properties. Moreover, the makeup and mechanical properties of these portions of the implant are not designed to be adjusted or modified during a procedure for surgically placing the implant. To Applicant's understanding, no implants are known that allow a user to easily and conveniently adjust a mechanical property of an implant, or of just a portion of an implant during use (i.e., during a surgical implantation method), for example to match or complement a mechanical property of tissue that will be treated or supported by the implant.

According to the present description, implants are provided to include releasable reinforcement, meaning reinforcement that can be released as desired, i.e., selectively, by a user, during use, such as by a surgeon during a surgical procedure for placing the implant in a patient to support or treat soft tissue. By releasing the reinforcement, the mechanical property that the reinforcement (e.g., stiffness, rigidity, elasticity) imparts on the implant is eliminated.

The implant can be any type of surgical implant useful for any placement, and for treating any tissue or condition. Many varieties of surgical implants are known for treating conditions that include hernia, conditions of cardiac tissue, conditions of pelvic floor tissue (e.g., a condition of a urethra, bladder, vagina, uterus, anal sphincter, urinary sphincter), among others.

Implants described herein include releasable reinforcement that allows a surgeon to adjust one or more mechanical properties of the implant, during surgery. The mechanical properties of the implant, or only a portion of the implant (especially a tissue support portion of the implant), can be selected to provide desired elasticity or strength in the implant, in a manner that selectively provides desired strength, tension, or support to tissue being supported or treated. For example, relating to an extension portion of an implant, the elasticity or stiffness (rigidity) of the extension portion may be reduced to adapt the extension portion to provide a desired level of support to prolapsed, weakened, or damaged soft tissue.

The described implants also allow for selection of mechanical properties of an implant on a smaller scale, i.e., selection of mechanical properties of a portion of an implant (e.g., a tissue support portion). Anatomical tissues and organs such as soft tissues (muscle, vagina, cardiac tissue, urethra and bladder tissue, ligaments, fascia) have mechanical properties that vary over the area of the tissue. One region of a ligament, muscle, or vagina may have a different level elasticity or strength, relative to a different (even nearby or adjacent) region of the same tissue or organ. As an even more specific example, vaginal tissue has mechanical properties such as flexibility, elasticity, and strength, that can vary at different locations of the vagina An anterior vaginal wall may exhibit mechanical flexibility (or rigidity) that changes along the length (proximal to distal) of the vagina from the apex to the external vaginal opening. This variation can be amplified or altered, moreover, in the event of a prolapse condition in the patient. The same variations can exist in tissue of a posterior vaginal wall. Mechanical properties such as elasticity, rigidity, etc., of these tissues may also vary in a lateral direction, e.g., from top to bottom or side to side.

Implants described herein include releasable reinforcement that allows a surgeon to account for and adjust to these intra-tissue variations in mechanical properties of a patient's tissue, during surgery. The mechanical properties of only a portion of the implant, especially a tissue support portion of the implant, can be selected to match or to complement the strength, rigidity, or flexibility, as well as intra-tissue variations of these properties, of tissue that will be contacted with the portion of the implant. Mechanical properties at different locations or regions of a tissue support portion of can be adjusted to cause one region of the tissue support portion to have a mechanical property that differs from an adjacent region, allowing for small-scale adjustment of the mechanical properties of the tissue support portion, to specifically accommodate intra-tissue variations in mechanical properties of tissue, e.g., vaginal tissue. Adapting one or more mechanical properties of different regions of the tissue support portion, to intra-tissue variation in the tissue (e.g., vaginal tissue), can provide improved support of the tissue, thereby improving the therapeutic effect of a treatment of the tissue by surgical placement of the implant.

In specific embodiments, the implant can be a Y-type implant adapted to treat vaginal prolapse, e.g., apical vaginal prolapse, non-apical vaginal prolapse, or a combination of these, by a sacrocolpopexy procedure. The implant includes releasable reinforcement, which allows a surgeon to select mechanical properties of a portion of the implant, especially a tissue support portion of the implant, based on the strength, rigidity, or flexibility, of vaginal tissue, as well as the intra-tissue variations of these properties. The described implants and methods provide a surgeon with the ability to provide differential tensioning, stiffness, and support to the anterior and posterior vaginal walls. This includes the ability to provide a different level of tensioning, stiffness, or support, to the anterior vaginal wall relative to the posterior vaginal wall. On a smaller scale, this also, or alternately, includes the ability to provide a different level of tensioning, stiffness, or support, to different regions of anterior vaginal tissue or different regions of posterior vaginal tissue; e.g., a different level of tensioning, stiffness, or support, at one region of an anterior (or posterior) vaginal wall relative to a different region of the anterior (or posterior) vaginal wall.

Also described herein are new methods for using surgical implants that include releasable reinforcement. The methods involve identifying tissue to be supported; providing the implant, which includes the releasable reinforcement; and adjusting a mechanical property (tensioning, stiffness, or support) of the implant or a portion of the implant by releasing the releasable reinforcement. Implants useful for performing the method can be any surgical implant that includes releasable reinforcement as described.

According to certain embodiments, the method can include treating apical or non-apical prolapse using an implant as described, e.g., a Y-shaped implant, that includes releasable reinforcement. The releasable reinforcement may be present at an anterior vaginal leaf, a posterior vaginal leaf, a sacral leaf, or two or more of these. In use, the implant can be used to treat vaginal prolapse, with the releasable reinforcement being used to select one or more mechanical properties of the implant, e.g., of a portion of the implant. The releasable reinforcement may be used to provide different levels of tensioning, stiffness, or support, in one leaf of the implant relative to a second leaf of the implant, such as a different level of tensioning, stiffness, or support, in an anterior vaginal leaf relative to a posterior vaginal leaf Additionally or alternately, the releasable reinforcement may be used to provide different levels of tensioning, stiffness, or support, in one region of one leaf of the implant, relative to a different region of the same leaf of the implant, such as a different level of tensioning, stiffness, or support, in one region of an anterior vaginal leaf relative to a different region of the anterior vaginal leaf.

According to exemplary methods, the condition of tissue of a patient can be observed, and a surgeon can assess the strength or flexibility of the tissue, or regions of the tissue, and consequent need for added support of the tissue by an implant. The surgeon may then determine the level of certain desired mechanical properties of an implant to be placed to support the tissue, including level of support, tension, or flexibility (or rigidity) of an implant, of a portion (leaf) of an implant, or of different regions of a portion (leaf) of the implant. Upon determining the desired mechanical properties of the implant or portions of the implant, the surgeon can then selectively release the releasable reinforcement of the implant to provide desired mechanical properties of the implant, portion of implant, or region of a portion of implant. These adjustments, by releasing the releasable reinforcement, may be made during a surgical procedure, after assessing the condition of tissue to be supported, either before, during, or after surgically attaching the implant or portions thereof to relevant tissue.

As used herein, the term "distal," with reference to a patient's anatomy or a device, a portion of a device, or a method described herein, refers to a direction toward a posterior of the patient, e.g., toward a sacrum relative to a vagina or uterus, and the term "proximal," with reference to a patient's anatomy or a device or method described herein, refers to a direction toward an anterior of the patient, e.g., in a direction toward vaginal tissue or a urethra relative to a sacrum.

The term "removable" as used herein, such as with reference to a releasable reinforcement (filament, elongate stiffener) or an adhesive that is removable, refers to structure that is incorporated into an implant material in a manner by which the structure will remain in place at the implant material during use of the implant, i.e., during surgical placement of the implant, but that can selectively be partially, substantially, or completely removed from the implant material by applying a force on the structure (with or without disrupting the structure of the releasable reinforcement by cutting) in a manner that does not as a practical matter cause undue damage to the implant material (or an implant thereof)—i.e., in a manner that does not cause or require tearing, ripping, cutting, or another form of damage to the implant material to an extent that the implant material is no longer useful for surgical implantation. Optionally, as part of removing the releasable reinforcement structure, the structure or the implant material may be intentionally cut at one or multiple locations, in a manner that does not cause the implant material to be unsuitable for surgical implantation.

In one respect, the invention relates to a surgical implant that includes implant material and releasable reinforcement located at the implant material. The releasable reinforcement can be selectively released to affect a mechanical property of the implant material at the location of the releasable reinforcement.

In another aspect, the invention relates to a method of treating a patient. The method includes: providing a surgical implant material comprising implant material comprising releasable reinforcement, wherein the releasable reinforcement can be selectively released to affect a mechanical property of the implant material at the location of the releasable reinforcement; and during a surgical procedure to place the surgical implant in a patient, releasing the reinforcement to affect a mechanical property of the implant material at the location of the releasable reinforcement.

BRIEF DESCRIPTION OF THE DRAWINGS

All drawings are schematic and not to scale.

DETAILED DESCRIPTION

According to the present description, implants and methods are provided, wherein the implant includes releasable reinforcement, meaning reinforcement that can be released as desired, i.e., selectively, by a user, during use, such as by a surgeon during a surgical procedure for placing the implant in a patient to support or treat soft tissue. The implant can be any type of implant, useful for any type of surgical placement, and for treating any physical condition and any type of tissue. Exemplary implants can be designed for treating a pelvic condition or pelvic tissue, e.g., tissue of a vagina, vaginal apex, rectum, urethra, bladder (including bladder neck), uterus, sphincter (e.g., anal sphincter, urinary sphincter), muscle (e.g., levator muscle). Alternative implants may be designed for treating cardiac tissue, herniated tissue, and other muscle and soft tissues.

The implant can be any of various types of implants that are presently known, or that may be developed in the future, e.g., for treating a soft tissue. Countless varieties of implant types, and specific implant designs and structures, are known, including implants that are elastic, inelastic, shaped (e.g., in the form of a strip), adjustable in size, bioabsorbable (partially or completely), synthetic, biologic (e.g., porcine, cadaveric), etc. Exemplary implants can be designed to contact or support pelvic tissue (vagina, bladder (including a bladder neck), urethra, uterus, muscle (e.g., levator), rectum, sphincter (e.g., anal sphincter or urinary sphincter) fascia, or other tissue), a hernia, cardiac tissue, or other muscle or soft tissue in need of support or repair.

Examples of useful implant designs are described in United States Patent and Patent Publication Documents that include the following: U.S. Pat. Nos. 8,702,585; 7,351,197; 7,407,480; 7,422,557; 7,500,945; 7,722,527; 7,905,825; 7,993,261; 8,070,672; 8,109,866; 8,211,005; 8,388,514; 8,517,914; 8,585,576; 8,597,173; 8,777,836; 8,777,837; 8,834,350; 8,932,201; 8,952,276; and 9,144,426; and U.S. Publication No. 2002/0028980, published Mar. 7, 2002; U.S. Publication No. 2011/0015477, published Jan. 20, 2011; 2014/0073850, published Mar. 13, 2014; 2013/0109910, published May 2, 2013; 2015/0112123, published Apr. 23, 2015; 2014/0228624, published Aug. 14, 2014; 2011/0257472, published Oct. 20, 2011; 2010/0298630, published Nov. 25, 2010; 2014/0309485, published Oct. 16, 2014; 2012/0323067, published Dec. 20, 2012; 2012/01884805, published Jul. 19, 2012; 2014/0357941, published Dec. 4, 2014; and 2015/0374408, and published Dec. 31, 2015; the entirety of each of these references being incorporated herein by reference.

According to the present description, an implant can include general features of an implant, and additionally includes releasable reinforcement as described herein, meaning one or multiple structural components that provide for reinforcement of a mechanical property, and that can be selectively released (e.g., removed or disabled) during use. The releasable reinforcement is placed at a location of implant material to cooperate with at least a portion of the implant (e.g., a tissue support portion, an extension portion, or the like) in a manner that affects one or more mechanical properties of the implant material. A mechanical property that is affected by the releasable reinforcement may be, for example, stiffness (e.g., rigidity), elasticity, or tension in the implant material. A releasable reinforcement may be a stiff and rigid structure (e.g., relative to the implant material) that, when included in the implant material, increases the rigidity of an implant material. Alternately, a releasable reinforcement may be both flexible (e.g., exhibits a flexibility similar to that of the implant material) and longitudinally elastic (e.g., as with a rubber band) to affect (i.e., reduce, marginally or slightly) an elasticity of the implant material in one dimension, such as along a length or a width. Still otherwise, the releasable reinforcement may be flexible and relatively inelastic (such as a braided surgical suture, thread, or polymeric monofilament strand) to also affect (e.g., reduce, more substantially) the elasticity of the implant material in a single dimension such as a length or a width.

Stiffness refers to the relative flexibility or rigidity of an implant material in a dimension perpendicular to a dimension of a plane of the implant material, i.e., in a dimension perpendicular to a length and width of the implant material, meaning the extent to which the material resists deformation (e.g., bending) in response to a force applied in a dimension perpendicular to a dimension of a plane of the implant material. Stiffness relates to rigidity and flexibility of the implant material, in that the more flexible or pliable a material is, the less stiff (rigid) the material is. Stiffness is a mechanical property that can be measured by known tests, and can be expressed as newtons per meter (pounds per inch).

Elasticity refers to the elastic modulus (aka tensile modulus), which is a measure of the resistance of the implant material to being deformed elastically (i.e., non-permanently) when stretched in a direction of the plane of the material, e.g., along a width or a length. Elasticity is a mechanical property that can be measured by known tests, and can be expressed in terms of stress/strain, where stress is the force causing the deformation divided by the area to which the force is applied, and strain is the ratio of the change in some length parameter caused by the deformation to the original value of the length parameter.

The releasable reinforcement is a structure that is incorporated into or attached to the implant material of a surgical implant, e.g., along a length in one direction (e.g., length or width), to affect (i.e., modify) a mechanical property of the implant material. When the implant is being used, i.e., placed surgically in a patient, the releasable reinforcement can be released (e.g., removed, diminished, or disabled) to reduce or eliminate the mechanical property that is otherwise provided by the releasable reinforcement on the implant material. Releasing the releasable reinforcement may be perform~ as one example, by removing the releasable reinforcement (or a portion thereof) from the implant material, i.e., physically taking the releasable reinforcement away from contact with the implant material. Removing the releasable reinforcement eliminates the effect of a mechanical property of the releasable reinforcement (e.g., stiffness of a rigid reinforcement incorporated into the implant material to increase its stiffness) on the mechanical properties of the implant material. Alternately, releasing the releasable reinforcement may be accomplished by a user disrupting the structure of the releasable reinforcement to eliminate the mechanical effect that the releasable reinforcement otherwise places on the implant material, such as by breaking or cutting the releasable reinforcement along its length, or disconnecting the releasable reinforcement from an attachment to the implant material, to effectively reduce or eliminate the physical effect that the releasable reinforcement would otherwise impart toward a mechanical property of the implant material.

The ability to change a mechanical property of an implant or a portion of an implant (e.g., a tissue support portion or an extension portion) can be useful or advantageous to a surgeon. In one respect, a surgeon may wish to adjust a mechanical property of an implant or a portion of an implant, depending on the level of support, elasticity, or tension desired in an implant or implant portion, such as to adjust an elasticity of an extension portion based on factors determined during surgery.

In another respect, a surgeon may wish to adjust properties of a portion of an implant, based on variations identified in tissue that will contact the portion of the implant. Biological tissue can have mechanical properties that vary based on location over an area of tissue or an organ. As just one example, vaginal tissue has mechanical properties that may be different depending on location. In some instances, an anterior vaginal wall may have less strength or support as compared to a posterior vaginal wall, especially if the tissue is prolapsed. Additionally or alternately, on a smaller scale, one vaginal wall (e.g., an anterior wall or a posterior vaginal wall) may exhibit mechanical flexibility (or rigidity) that changes along a length of the vagina from the apex to the external vaginal opening. This variation can be increased or altered in the event of a condition of prolapse. Mechanical properties such as elasticity, rigidity, etc., of these tissues may vary in a longitudinal direction and laterally. As described herein, implants that include releasable reinforcement can be useful for a surgeon to accommodate these intra-organ and intra-tissue variations, during surgery, to allow mechanical properties of the implant (especially a tissue support portion of the implant) to be selected to match or complement those of an organ or tissue that will be contacted and supported with an implant or with a particular portion of an implant.

Certain examples of implants that can be adapted to include releasable reinforcement as described herein are surgical implants useful for treating vaginal prolapse in a female patient, e.g., prolapse of non-apical anterior or posterior vaginal tissue such as a cystocele or a rectocele, etc.; prolapse of apical vaginal tissue, meaning vaginal vault prolapse; or a combination of these. See, e.g.: U.S. Pat. Nos. 6,884,212; 7,351,197; 7,407,480; 7,500,945; 8,597,173; 8,834,350; 8,932,201; 8,952,276; and PCT publication WO 2014/149612 (PCT/US2014/019871), the entireties of these documents being incorporated herein by reference. Examples of implants as described in these documents include a portion of implant material that is adapted to be placed at and optionally secured to vaginal tissue, e.g., tissue of an anterior vaginal wall, of a posterior vaginal wall, or a vaginal apex (i.e., a tissue support portion). These implants also generally include an extension portion, which extends from the tissue support portion and is adapted to pass through or attach to tissue in a pelvic region to support the tissue support portion. A tissue support portion, extension portion, or both, of any of these implants, can be modified to include releasable reinforcement as described herein, for use in methods as described herein, e.g., to modify one or more mechanical properties of a tissue support portion based on one or more mechanical properties of tissue being supported by the tissue support portion.

One type of implant that is useful for treating apical vaginal prolapse is the type of implant sometimes referred to as a "y-mesh" or "y-type" implant. See, e.g., patent documents U.S. Pat. No. 6,884,212 (Thierfelder et al.); U.S. Pat. No. 8,952,276 (Young et al.), and PCT publication WO 2014/149612 (PCT/US2014/019871. These implants are known to be useful in performing a sacral colpopexy, by which a distal portion of an implant is generally placed surgically at tissue at a region of a sacrum, and a proximal portion is located during use at 25 a region of vaginal tissue. The distal portion includes a sacral leaf (or "appendage"). Example proximal portions of these implants can include an anterior vaginal leaf (or "appendage"), and a posterior vaginal leaf (or "appendage"). In use, the anterior vaginal leaf can be placed in contact with and surgically secured to anterior vaginal tissue and can thereby be effective to support the anterior vaginal tissue in a surgical treatment of non-apical anterior vaginal prolapse. The posterior vaginal leaf can be placed in contact with and surgically secured to posterior vaginal tissue and can thereby be effective to support the posterior vaginal tissue as part of a surgical treatment for non-apical posterior vaginal prolapse. Alternately, or in addition, the combined anterior vaginal leaf and posterior vaginal leaf can be placed at tissue of a vaginal apex or vaginal cuff to support the vaginal apex in treating apical prolapse. In these treatments, the sacral leaf is suspended by attachment to a posterior location such as at tissue of a region of sacral anatomy, to thereby support the proximal portion of the implant and the vaginal tissue that is attached to the proximal portion of the implant.

The anterior vaginal leaf of the implant can be a piece of surgical implant material that is adapted to function as a tissue support portion by being placed in contact with vaginal tissue on an anterior portion of a vagina; the implant material can be surgically placed at and secured to the anterior vaginal tissue in a manner to support the tissue as a treatment for anterior vaginal prolapse, e.g., cystocele. When the anterior vaginal leaf is placed in contact with and surgically secured to the anterior vaginal tissue, the anterior vaginal leaf can be effective to support the anterior vaginal tissue as a treatment for anterior vaginal prolapse. Similarly, the posterior vaginal leaf of the implant can be a piece of surgical implant material that is adapted to function as a tissue support portion by being placed in contact with vaginal tissue on a posterior portion of a vagina; the implant material can be surgically placed at and secured to the posterior vaginal tissue in a manner to support the tissue as a treatment for posterior vaginal prolapse, e.g., rectocele. According to the present description, one or both of these tissue support portions can include releasable reinforcement.

An implant, designed for any of surgical purpose, can include one or more supportive portions (e.g., tissue support portions, extension portions, or other portions or regions of a device designed to contact or support tissue) constructed of surgical implant material adapted to contact or support tissue, for example tissue in a pelvic region of a patient The surgical implant material can be a generally planar, flexible, porous implant material adapted to be placed surgically to support tissue, e.g., pelvic tissue, vaginal tissue, etc. Many examples of flexible implant materials are known and commercially available, including porous (e.g., mesh) materials that are prepared by assembling strands of fibers such as polymeric monofilaments into a flexible planar woven, non-woven, or knit, fabric.

Suitable implant materials are well known and examples are sold commercially for use as surgical implant materials for supporting anatomical tissue. These include woven, knitted, extruded, or other open pore (porous) materials made from connected strands, fibers, threads, filament (e.g., monofilament), treated film, or the like, which may be natural or synthetic. Exemplary implant materials include woven, non-woven (but still fibrous or filamentary), knitted, or other materials having inter-linked, tied, or otherwise connected filaments or fibers that form multiple fiber junctions and multiple regular or randomly sized and spaced apertures. Implant materials made of monofilament fibers or multi-filament fibers are helpful in treating vaginal prolapse, as are materials that include two or more types of different (monofilament, multi-filament, or a combination) fibers assembled together to prepare an implant material. The fiber junctions may be formed by weaving, bonding (e.g., adhesive bonding, thermo-bonding, etc.), tying, ultrasonic welding, knitting, or other junction-forming techniques, including combinations thereof. The size of the resultant openings, pores, apertures, or fenestrations, etc., is sufficient to allow tissue in-growth and fixation of the open pore implant material at contacted tissue after the implant is placed at an anatomical location such as vaginal tissue. As an example, not intended to be limiting, apertures of an open pore implant material may take a form of elliptical, square, circular, rectangular, or diamond shaped apertures having a diagonal or diameter dimension in a range of about 0.040 inches (1.016 mm) to about 0.055 inches (1.397 mm).

Strands, layers, or filaments, etc., of an open pore implant material can be of any material useful to form a surgical implant. Suitable natural and polymeric materials are biocompatible, optionally bioabsorbable, and may be coated to encourage tissue ingrowth or prevent infection. Examples include nylon, polyethylene terephthalate, polyolefins such as polypropylene and polyethylene, poly-L-lactide (PLLA), polyethylene glycol (PGA), polyester, and any combination of materials. Depending on the desired treatment, the polymer may be absorbable, non-absorbable, or resorbable. Example of commercially available implant materials include those sold under the trade names Prolene™, Deldene™, and Marlex™ implantable materials. Yet another example is woven polypropylene monofilament, knitted with a warp tricot.

Implants of the present description include releasable reinforcement Exemplary releasable reinforcement can be in the form of an elongate structure such as a filament (e.g., a suture, thread, monofilament) that extends from one location of an implant or implant material to another (e.g., along a length, or along a width, or diagonally), and that is connected to the implant material at one or multiple locations.

A filament or other releasable reinforcement can be made of any material that is biocompatible. For convenience or consistency, the releasable reinforcement may be made of a material that is also used to construct the implant material of a particular surgical implant, e.g., polypropylene or any other biologically compatible polymeric, synthetic, or natural implant material. A filament (or other reinforcement) can be equal in size and strength compared to other filaments made to construct the implant material, or could instead have a larger cross-sectional area to provide additional strength, stiffness, or both. Multiple releasable reinforcement filaments of an implant can have the same or different sizes, stiffness, or strength. Optional color coding could be applied to the filament (or other releasable reinforcement) to allow for easy identification and differentiation between the stronger (or less flexible) reinforcements and less strong (or more flexible) reinforcements. Color coding of the releasable reinforcement can also be useful to differentiate between different implant portions (e.g., leafs), by providing differently-colored releasable reinforcement on a sacral leaf, a first vaginal leaf: a second vaginal leaf, or an extension portion.

A connection of the releasable reinforcement to the implant material serves to incorporate one or more physical properties of the reinforcement into the implant material, but may optionally be easily disrupted so that the filament (or other releasable reinforcement) is removable from the implant material during use. Generally, a filament included in and attached to an implant material will increase a tensile strength of the implant material, and will decrease the elasticity of the implant material. The connection between the implant material and the filament may be any form of connection, such as by a knot, an adhesive, heat bonding, ultrasonic bonding, etc. As one example, a suture (or other filament) that is woven into (passed through holes of) a porous implant material along a length or width dimension, and is connected to the implant material at two or more locations, will affect the tensile strength or elasticity of the implant material in the dimension. The filament can be passed through the holes of the implant material in a manner such that, when one or more of the connections are released, the filament can be easily pulled out of its engagement with the implant material and physically removed from the implant material.

To release a releasable reinforcement in the form of a filament, as one example, the filament can be disconnected from the implant material and pulled out of and away from the implant material. Removing the filament will reduce the strength of the implant material, allowing the implant material to be more easily elongated or stretched. Removing the filament may additionally or alternately decrease the elasticity of implant material, reducing the level of resistance of the implant material to being elastically deformed.

In addition to, or as an alternative to a filament as a releasable reinforcement, an implant as described can include releasable reinforcement in the form of a relatively more strong and rigid structure, referred to as elongate stiffener. An elongate stiffener is an elongate, relatively stiff (i.e., stiffer than a suture, monofilament, or implant material), solid, continuous structure (e.g., polymeric) that is relatively inelastic (relative to the implant material) along a length (i.e., a substantially fixed length), and that is relatively stiff, resistant to bending, and resistant to stretching or compression as compared to an implant material. An elongate stiffener can be included in or on an implant material by being placed along a length of the implant material, extending from one location of an implant or implant material, to another, optionally being connected to the implant material at one or multiple locations, and optionally passing through one or more holes or openings of the implant material. The (optional) connections serve to incorporate one or more physical properties of the reinforcement into the implant material, but may optionally be easily disrupted to that the elongate stiffener is removable from the implant material during use. For example, an elongate stiffener that passes through openings in a porous implant material along a length or width dimension, and is optionally connected to the implant material at two or more locations, will affect the stiffness of the implant material in a dimension that is perpendicular to the length and width. Generally, an elongate stiffener included in and optionally attached to an implant material will increase a stiffness of the implant material, will decrease the flexibility of the implant material, and may also optionally reduce the elasticity of the implant material. The optional connection between the implant material and the elongate stiffener may be any form of connection, such as by an adhesive, heat bonding, ultrasonic bonding, etc., and may optionally be overcome by a user without damaging the implant material, i.e., may be removable.

To release a releasable reinforcement in the form of an elongate stiffener, as one example, the elongate stiffener can be disconnected from the implant material and pulled out of and away from the implant material. Removing the elongate stiffener will reduce the stiffness (rigidity) of the implant material, increasing the flexibility, and allow the implant material to be more easily bent along its width and length to allow the material to be conformed to tissue.

Referring now to FIGS. 1A, 1B, 1C, and 1D, illustrated are first examples of implant that include releasable reinforcement 12. At FIG. 1A, implant 2 is a Y-shaped implant that includes anterior portion 26, distal portion 44, and junction 6. Anterior 15, portion 26 includes anterior vaginal leaf 14 and posterior vaginal leaf 16. Distal portion 44 includes sacral leaf 10. All three of anterior vaginal leaf 14, posterior vaginal leaf 16, and sacral leaf 22, meet at junction 6, which can be any form of a three-way connection that joins a proximal end of sacral leaf 22 to a distal end of anterior vaginal leaf 14 and a distal end of posterior vaginal leaf 16. Implant 2, and all of anterior portion 26, distal portion 44, and their respective vaginal and sacral leafs 14, 16, and 10, are all constructed of implant material 4 as shown at various cut-in representations of the implant material; while not illustrated, implant material 4 also makes up the balance of all leafs of implant 2; the illustrations do not specifically show implant material 4 over the entire area of the implant, because this allows reinforcement 12 to be clearly shown.

Figure 1A:
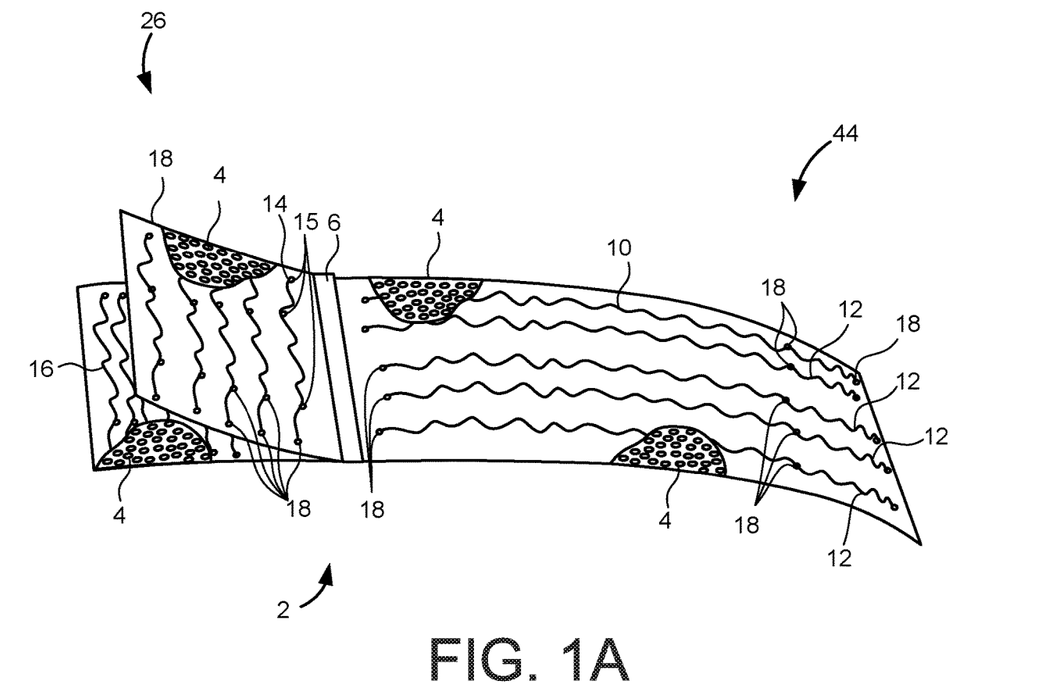
FIGS. 1A, 1B, 1C, 1D, 2A, and 2B shows examples of implants that include releasable reinforcement.

Referring still to FIG. 1A, sacral leaf 10 extends from junction 6 in a distal direction to a distal end of implant 2, and is adapted to be attached to tissue at a region of sacral anatomy. A first vaginal leaf, e.g., an anterior vaginal leaf 14, extends from junction 6 in a proximal direction and is adapted to support vaginal tissue, e.g., anterior vaginal tissue. A second vaginal leaf, e.g., a posterior vaginal leaf 16, extends from junction 6 in a proximal direction and is adapted to be attached to vaginal tissue, e.g., posterior vaginal tissue. Each leaf, independently, has a width, and each of the widths can be the same or different from each other. According to these implant embodiments, each of the two vaginal leafs can be of a single density (material weight) and in the form of a single ply of implant material (see FIG. 1). The sacral leaf can also be of a single ply and can exhibit the same single density material weight as the vaginal leafs. Alternately (see FIG. 2), the sacral leaf can be made of a single ply that is of a double density (double material weight) relative to the two vaginal leafs; i.e., a total weight of the sacral leaf material may be twice the weight of a single density vaginal leaf.

Releasable reinforcement 12 is in the form of multiple filaments 12. At vaginal leafs 14 and 16, filaments 12 extend laterally, i.e., in a width direction. As illustrated, filaments 12 are connected (e.g., by knot, adhesive, or the like) to implant material 4 at various locations, 18, also designated by open circles. Each laterally-extending filament 12 of leafs 14 and 16 is connected, as illustrated, at four locations along the length of filament 12 (also along the width of each leaf). Each filament 12 of sacral leaf 10 extends longitudinally (i.e., along a length of sacral leaf 10) and is connected, as illustrated, at three locations along the length of filament 12.

Figure 1B:
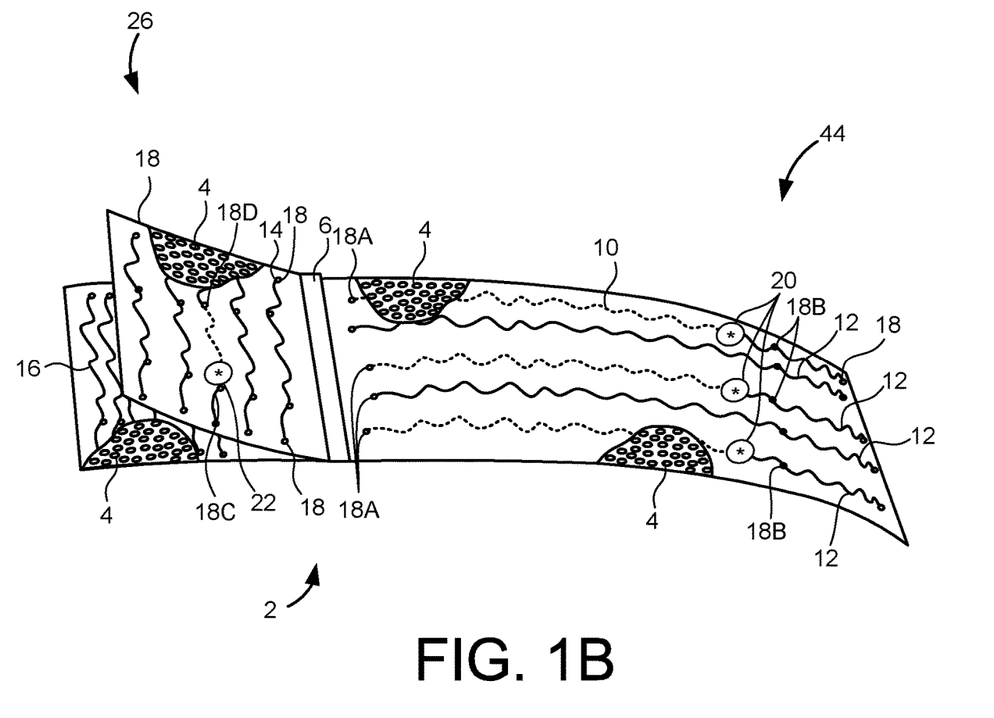

In use, to release a filament 12, a length of a filaments 12 of sacral leaf 10 between two connections 18A and 18B can be severed, e.g., at a single location of the cut, 20, as shown at FIG. 1B. This single cut (20) removes the effect of filament 12 on implant material 4, between the two connections 18A and 18B. That is, the effect of 20 filament 12 on the strength or elasticity of implant material 4 between the two connections 18A and 18B has been eliminated by cutting filament 12 a single time at location 20 (hence, these filaments 12 are shown in shadow). The remaining (cut) portions of filaments 12 do not need to be removed. Likewise, a single, central filament 12 of anterior vaginal leaf 14 has been released by cutting at location 20 between connections 18C and 18D. That filament 12 is also shown in shadow to indicate that it has been released and no longer imparts mechanical properties on implant material 4 of vaginal leaf 14, in a width direction, between connection 18C and 18D.

Figure 1C:
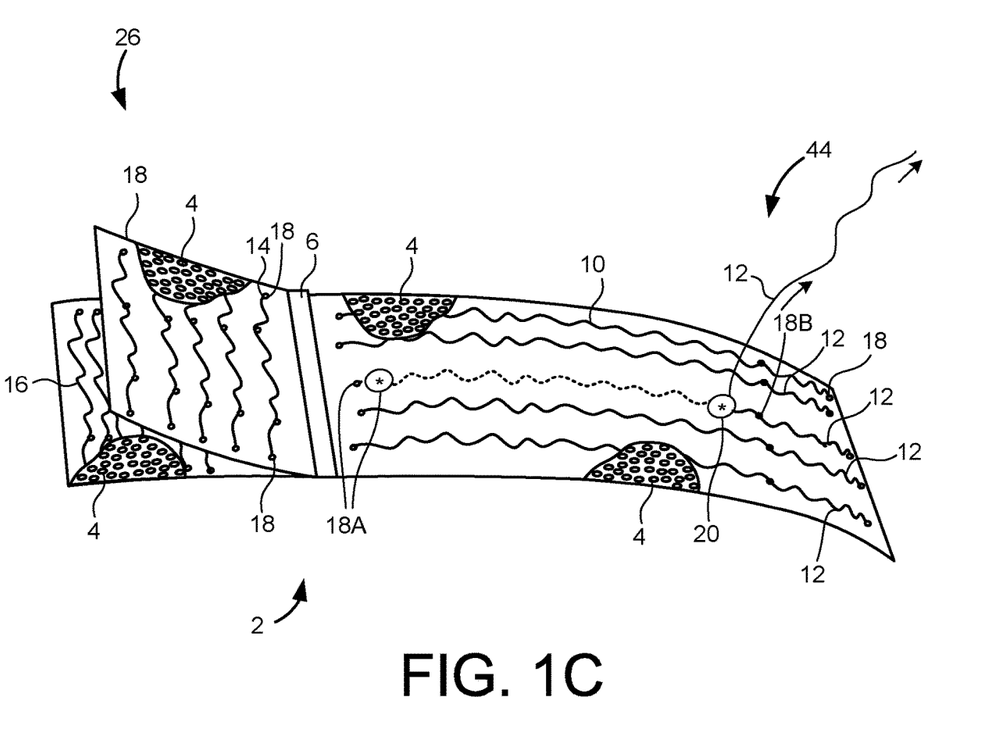

Alternately, to release a filament 12 of implant 2 of FIG. 1A, the filament may be removed by first cutting a portion of filament 12 (or implant material 4) to disconnect the filament 12 from implant material 4, followed by pulling the disconnected portion away from implant material 4. This is illustrated at FIG. 1C. As illustrated, filament 12 has been severed at two cut locations, 20, between connections 18A and 18B. After making cuts 20, filament 12 can be removed by pulling filament 12 away from implant material 4 as shown by arrows at FIG. 1C. The original location of the portion of filament 12 that has been removed is shown in shadow.

Figure 1D:
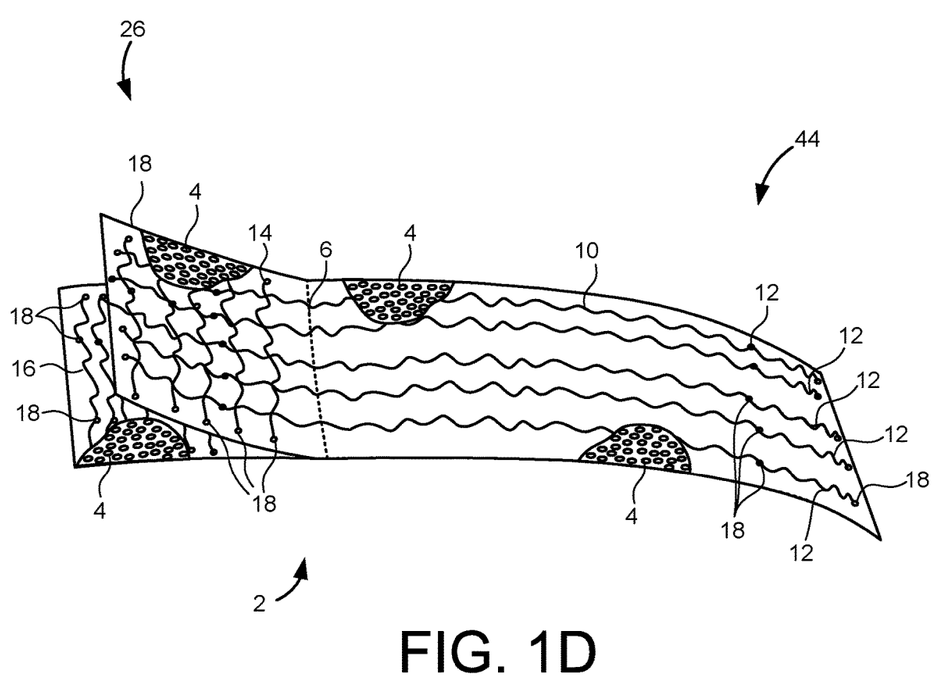

FIG. 1D shows an alternate embodiment of an implant 2. In this embodiment, one set of longitudinal filaments 12 extends essentially an entire length of implant 2, from a distal end of sacral leaf 10 to a proximal end of anterior vaginal leaf 14. Anterior vaginal leaf 14 also includes another set of lateral filaments 12 extending laterally (in a width direction). Posterior vaginal leaf 16 includes a set of lateral filaments 12 extending laterally (in a width direction), but does not include any longitudinal filaments extending in a lengthwise direction.

Figure 2A:
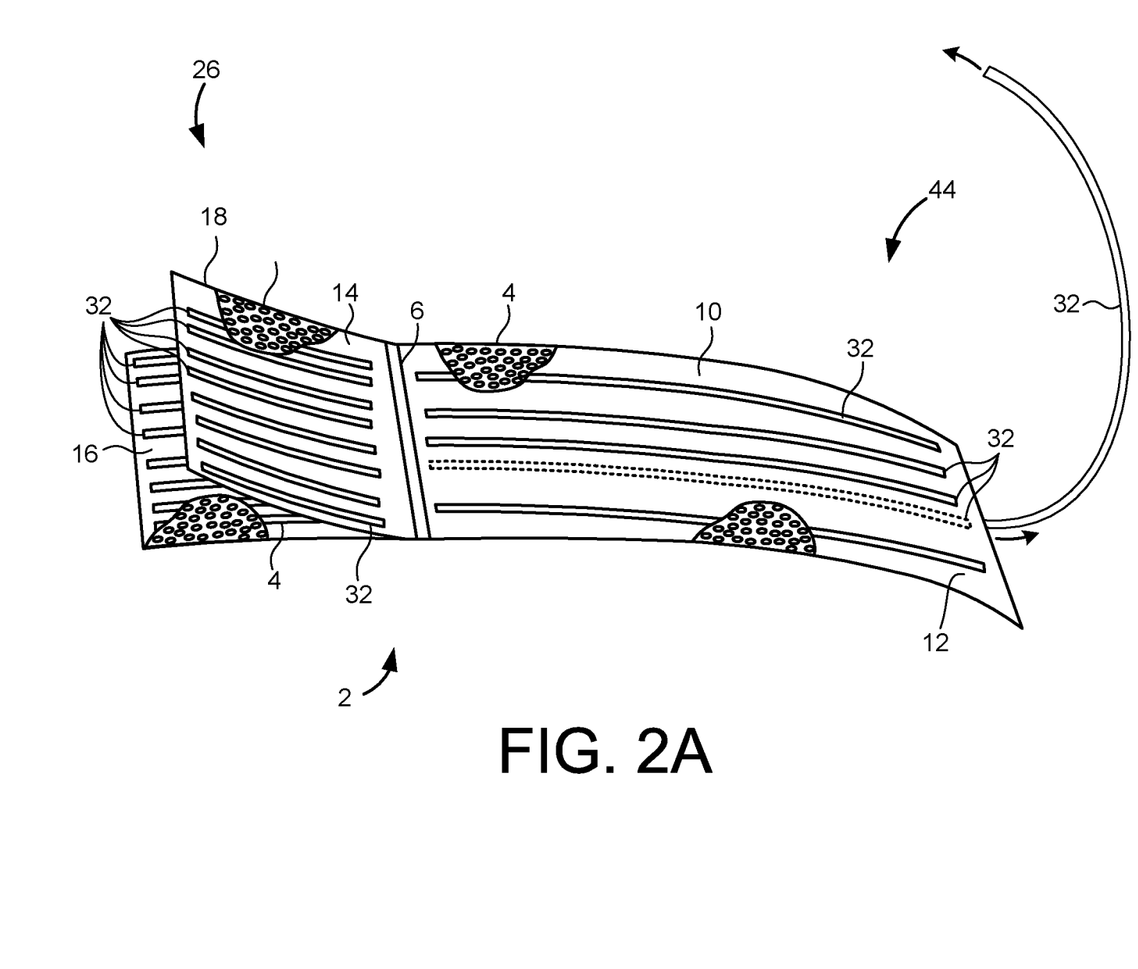
Figure 2B:
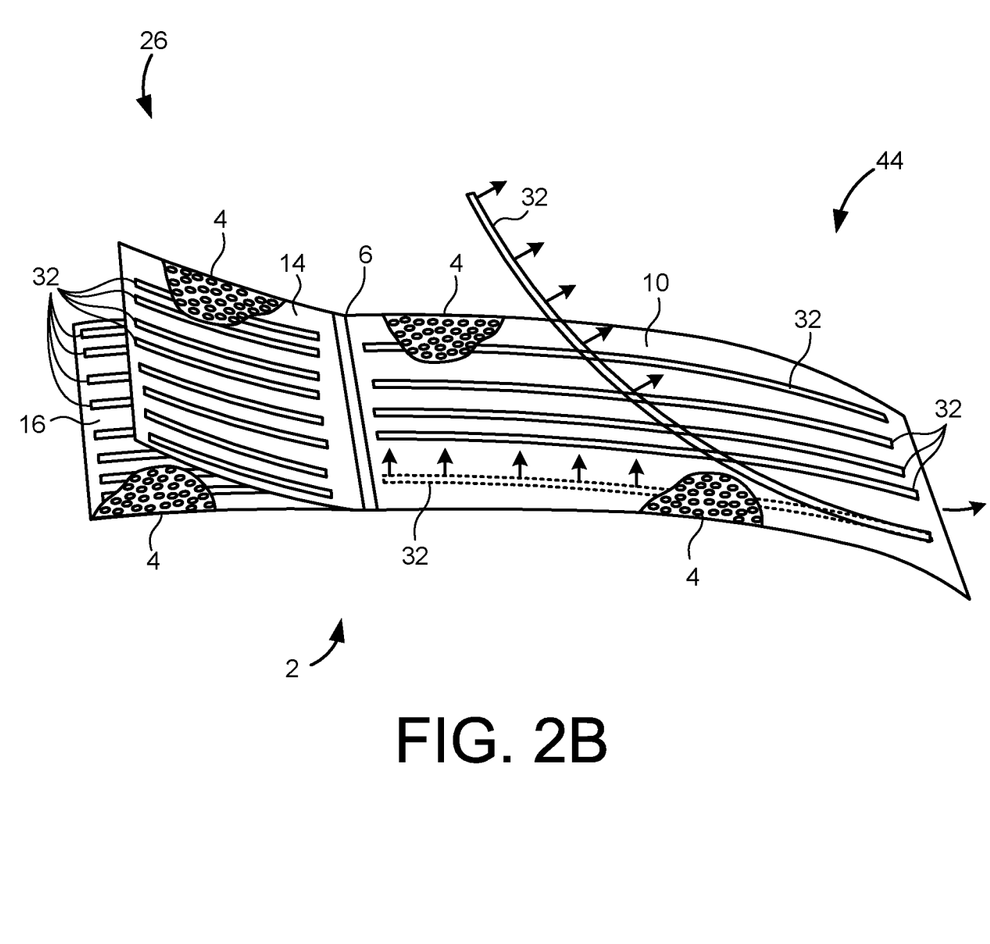

With reference now to FIGS. 2A and 2B, illustrated is a different example of an implant 2 that includes releasable reinforcement 32. Implant 2 is a Y-shaped implant that includes anterior portion 26; distal portion 44, and junction 6. Anterior portion 26 includes anterior vaginal leaf 14 and posterior vaginal leaf 16. Distal portion 44 includes sacral leaf 10. All three of anterior vaginal leaf 14, posterior vaginal leaf 16, and sacral leaf 22, meet at junction 6. Implant 2, and all of anterior portion 26, distal portion 44, and their respective vaginal and sacral leafs 14, 16, and 10, are all constructed of implant material 4 as shown at various cut-in representations of the implant material; while not illustrated, implant material 4 also makes up the balance of all leafs of implant 2; the illustrations do not specifically show implant material 4 at those locations, because this allows reinforcement 12 to be clearly shown.

Releasable reinforcement 32 of implant 2 of FIGS. 2A and 2B is in the form of multiple elongate stiffeners 32. Each of vaginal leafs 14 and 16 includes multiple elongate stiffeners 12 extending from a proximal end of the vaginal leaf to a distal end of the vaginal leaf near junction 6. Elongate stiffeners 32 may be incorporated into implant material 4 by being passed through openings of implant material 4 (not shown) or by another method such as by securing elongate stiffeners 32 to a surface of implant material 4 by use of a removable adhesive (see FIG. 2B).

In use, to release an elongate stiffener 32 from a leaf 10, 14, or 16, of implant 2 of FIG. 2A, the elongate stiffener may be disconnected from implant material 4 (if necessary) followed by pulling the disconnected elongate stiffener away from implant material 4. This is illustrated at FIG. 2A. As illustrated, elongate stiffener 32 has been pulled in a distal direction, in its entirety, from its original location (in shadow) within implant material 4, e.g., woven or threaded between openings of implant material 4. While not illustrated, any of the other elongate stiffeners 32 of implant 2 of FIG. 2A may be selectively removed in a similar manner, by a surgeon, to adjust the mechanical properties (e.g., stiffness) of one or more of leafs 10, 14, and 16, depending on the mechanical properties of tissue to which the leaf will be contacted, or depending on tension or strength of a leaf otherwise desired when implant 2 is placed at a surgical site.

FIG. 2B shows an alternate embodiment of implant 2 and elongate stiffeners 32. In this embodiment, elongate stiffeners 32 are placed on surfaces of leafs 10, 14, or 16, of implant 2, and secured with a removable adhesive, meaning an adhesive that causes the elongate stiffener to be removable as described herein. One or more of the elongate stiffeners 32 may be released by disconnecting the elongate stiffener from the surface of 15 implant material 4 by pulling the elongate stiffener in a direction away from the surface of implant material 4 (see arrows at FIG. 2B). As illustrated, elongate stiffener 32 has been pulled in a direction away from a surface of sacral leaf 10, in its entirety, and removed from its original location (in shadow) at the surface of implant material 4 of sacral leaf 10. While not illustrated, any of the other elongate stiffeners 32 of implant 2 of FIG. 2B may be selectively removed in a similar manner, by a surgeon, to adjust the mechanical properties (e.g., stiffness) of one or more of leafs 10, 14, and 16, depending on the mechanical properties of tissue to which the leaf will be contacted, or depending on tension or strength of a leaf otherwise desired when implant 2 is placed at a surgical site.

Embodiments of implants useful in methods as described include releasable reinforcement that can be used to adjust a mechanical property of an implant material. Exemplary implants include releasable reinforcement on one or more tissue support portions (e.g., an anterior vaginal leaf or posterior vaginal leaf) or extension portions (e.g., sacral leaf) of the implant. The releasable reinforcement can be released to disable the reinforcement, reducing or essentially eliminating the physical effect of the releasable reinforcement on the implant material. The implant may include multiple releasable reinforcement structures at various locations of an implant. Exemplary implants can include multiple releasable reinforcement structures extending along a width direction, a length direction, diagonally, or any combination of these, of a tissue support portion. The multiple structures can be removed, selectively, during surgery, to adjust the mechanical properties of the tissue support portion in a manner that provides desired or improved support, flexibility, or strength to various regions of the tissue support portion, optionally based on intra-tissue variations in strength, flexibility, or needed support, of the tissue to which the tissue support portion is to be attached.

Figure 3:
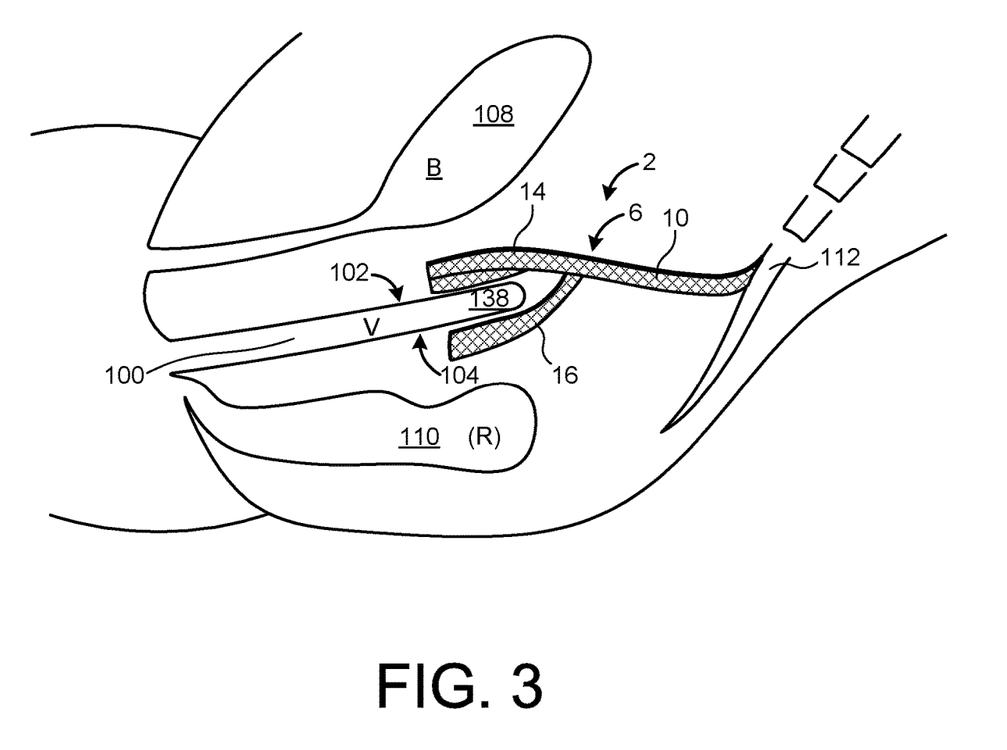
FIG. 3 shows an example of an implant as described, used in a method as described.

Referring now to FIG. 3 (side view), certain features of female anatomy that are relevant to methods of the present description, are illustrated. Illustrated anatomy includes vagina (V) 100, anterior vaginal tissue 102, posterior vaginal tissue 104, bladder (B) 108, rectum (R) 110, sacrum (S) 112 (i.e., a region of sacral anatomy that includes the sacral promontory and anterior sacral ligament, etc., none of which being specifically shown), and vaginal vault (i.e., vaginal apex) 120. The uterus of the patient has been removed.

A method of placing an implant as described may be performed by surgical techniques that include one or more steps of previously known sacrocolpopexy procedures, but modified as described herein to include a step of using releasable reinforcement to adjust mechanical properties of the implant based on mechanical, strength, or support properties of tissue at a surgical site. A procedure of the present invention can be useful for treating any tissue or condition of soft tissue, certain non-limiting examples including conditions of non-apical vaginal prolapse, apical prolapse, or a combination of non-apical and apical vaginal prolapse. For certain particular methods of treating a vaginal condition, a useful procedure can entail suspension of apical or non-apical vaginal tissue (e.g., anterior vaginal tissue or posterior vaginal tissue) to tissue at a region of sacral anatomy (e.g., the sacrum (bone itself), a nearby sacrospinous ligament, a uterosacral ligament, fascia at or near the sacrum, or an anterior longitudinal ligament at the sacral promontory), via a surgical implant. The surgical implant can be any surgical implant that will be determined to be useful to perform a method as described herein, which includes releasable reinforcement, and that allows for selectively releasing the releasable reinforcement during surgical placement of the implant. Examples of useful implants are described and illustrated herein.

According to example methods for treating vaginal tissue, a Y-shaped implant (e.g., as described) can be placed surgically with a first vaginal leaf being secured to anterior vaginal tissue, a second vaginal leaf being secured to posterior vaginal tissue, and the sacral leaf being secured at tissue in a region of sacral anatomy. Before placement of the two vaginal leafs, a surgeon can assess the mechanical properties of the anterior and posterior vaginal tissue. Either before, during, or after placement of the two vaginal leafs and securement of both leafs to vaginal tissue, a user (e.g., surgeon) can adjust the mechanical properties of different regions of each leaf by selectively releasing one or more of the releasable reinforcements.

More specific example steps of such a surgical method include to trim the two vaginal leafs as desired to fit anterior and posterior vaginal tissues. The surgeon can then determine the desired level of support and tension to separately apply to each of the anterior and the posterior vaginal tissues depending on the degree and type of the condition, e.g., cystocele, rectocele, or both. The surgeon can also determine whether any particular region of anterior vaginal tissue or posterior vaginal tissue requires differential support or tension relative to adjacent vaginal tissue. The relative amounts of support and tension can be achieved by selectively releasing one or more releasable reinforcements located at the anterior leaf, the posterior leaf, or both, of the implant. When desired mechanical properties of the implant and each leaf are achieved, the vaginal leafs of the implant can be secured to the vaginal tissue. During or after these steps, the surgeon can determine the desired amount of sacral tension to be placed in the sacral leaf and the sacral leaf can be attached to tissue at a region of the patient's sacral anatomy, e.g., the sacral promontory.

Useful methods may be performed through an abdominal incision, through a vaginal incision, or laparoscopically, and optionally by use of robotic surgical equipment. Examples of known methods that are different from those of the present description, but that may have one or more method steps in common, are described in United States Patent Application Publications 2002/0028980; 2010/0184805; 2014/0005471; 2015/0057491; 2013/0109910; and U.S. Pat. Nos. 8,109,867; 8,720,446; and 8,956,276, the entireties of these documents being incorporated herein by reference.

What is claimed is:

1. A surgical implant comprising:
an implant including a woven material made from fibers, the implant including a tissue support portion and an extension portion extending from the tissue support portion; and
a first releasable reinforcement disposed on the tissue support portion extending in a first direction and a second releasable reinforcement disposed on the extension portion extending in a second direction, the second direction being perpendicular to the first direction,
wherein the first releasable reinforcement is formed of a non-absorbable material and is configured to be selectively released from the implant to affect a mechanical property of the tissue support portion of the implant,
wherein the second releasable reinforcement is configured to be selectively released from the implant to affect a mechanical property of the extension portion of the implant,
wherein the first releasable reinforcement includes three filaments extending along a first dimension of the implant, wherein not one of the three filaments crosses another of the three filaments,
wherein the second releasable reinforcement includes three filaments extending along a second dimension of the implant, the second dimension being substantially perpendicular to the first dimension, and wherein not one of the three filaments extending along the second dimension crosses another of the at least three filaments extending along the second dimension.

2. The implant of claim 1, wherein at least one of the three filaments of the first releasable reinforcement is attached to the implant at two or more locations along the length of the filament.

3. The implant of claim 1, wherein
the implant is a porous planar material that includes openings,
at least one of the three filaments of the first releasable reinforcement or at least one of the three filaments of the second releasable reinforcement passes through one or more of the openings.

4. The implant of claim 1, wherein the first or second releasable reinforcement has a stiffness that is greater than a stiffness of the implant.

5. The implant of claim 1, wherein
the implant comprises a mesh prepared from strands, and
at least one of the three filaments of the first releasable reinforcement or at least one of the three filaments of the second releasable reinforcement has a diameter that is greater than a diameter of the strands.

6. The implant of claim 1, wherein two of the three filaments of the first releasable reinforcement have different stiffnesses, different diameters, or both.

7. The implant of claim 1, wherein the implant is a Y-shaped implant, the Y-shaped implant comprising:
an extension portion including a sacral leaf having a proximal sacral leaf end at a junction and a distal sacral leaf end; and
tissue support portions including:
a first vaginal leaf including a first vaginal leaf proximal end and a first vaginal leaf distal end, the first vaginal leaf distal end being connected to the proximal sacral leaf end at the junction, and
a second vaginal leaf including a second vaginal leaf proximal end and a second vaginal leaf distal end, the second vaginal leaf distal end being connected to the proximal sacral leaf end at the junction.

8. The implant of claim 7, wherein the first or second releasable reinforcement is located at the first vaginal leaf, the second vaginal leaf, or both.

9. The implant of claim 7, wherein the sacral leaf, the first vaginal leaf, and the second vaginal leaf, are each constructed of mesh.

10. The implant of claim 1, wherein the first releasable reinforcement extending substantially linearly when disposed on the tissue support portion.

11. The implant of claim 1, wherein the support portion defines an axis, the first direction being parallel to the axis.

12. A method of treating a patient, the method comprising:
providing a surgical implant including a woven material made from fibers, a first releasable reinforcement, and a second releasable reinforcement, the implant includes a tissue support portion and an extension portion extending from the tissue support portion, the first releasable reinforcement includes three filaments extending along a first dimension of the implant, wherein not one of the three filaments crosses another of the three filaments, the second releasable reinforcement includes three filaments extending along a second dimension of the implant, the second dimension being substantially perpendicular to the first dimension, and wherein not one of the three filaments extending along the second dimension crosses another of the three filaments extending along the second dimension; and releasing, prior to completing a surgical procedure to place the surgical implant into a body of the patient, at least one of the three filaments of the first releasable reinforcement and the three filaments of the second releasable reinforcement to affect a mechanical property of the implant of at least one of the tissue support portion and the extension portion.

13. The method of claim 12, wherein the method comprises treating a pelvic condition.

14. The method of claim 12, wherein the method comprises treating vaginal prolapse.

15. An implant comprising:

an implant including a tissue support portion, a first extension portion extending from the tissue support portion and a second extension portion extending from the tissue support portion, the implant having a first end portion and a second end portion, a length extending between the first end portion and the second end portion defining a longitudinal axis;

a first releasable reinforcement coupled to the tissue support portion, the first releasable reinforcement extending substantially linearly and substantially parallel to the longitudinal axis, the first releasable reinforcement is formed of a non-absorbable material;

a second releasable reinforcement coupled to the extension portion, the second releasable reinforcement extending substantially linearly and substantially perpendicular to the longitudinal axis; and a third releasable reinforcement coupled to the second extension portion, the third releasable reinforcement extending substantially linearly and substantially perpendicular to the longitudinal axis.

16. The implant of claim 15, wherein the implant is formed of a mesh and includes openings, at least one of the first releasable reinforcement and the second releasable reinforcement passes through one or more of the openings.

17. The implant of claim 15, wherein at least one of the first releasable reinforcement and the second releasable reinforcement has a stiffness that is greater than a stiffness of the implant.

18. The implant of claim 15, wherein the implant comprises a mesh prepared from strands, and at least one of the first releasable reinforcement and the second releasable reinforcement has a diameter that is greater than a diameter of the strands.

* * * * *